(12) United States Patent
Panayi (10) Patent No.: US 8,513,597 B2
(45) Date of Patent: *Aug. 20, 2013

(54) ATOM PROBE

(75) Inventor: Peter Panayi, Norfolk (GB)

(73) Assignee: Cameca Instruments, Inc., Mahwah, NJ (US)

(*) Notice: Subject to any disclaimer, the term of this patent is extended or adjusted under 35 U.S.C. 154(b) by 707 days.

This patent is subject to a terminal disclaimer.

(21) Appl. No.: 11/917,663

(22) PCT Filed: Jun. 16, 2006

(86) PCT No.: PCT/GB2006/002209
§ 371 (c)(1),
(2), (4) Date: Sep. 25, 2009

(87) PCT Pub. No.: WO2006/134380
PCT Pub. Date: Dec. 21, 2006

(65) Prior Publication Data
US 2010/0148060 A1    Jun. 17, 2010

(30) Foreign Application Priority Data

Jun. 17, 2005 (GB) .................................. 0512411.0
Jul. 11, 2005 (GB) .................................. 0514216.1

(51) Int. Cl.
*H01J 49/00* (2006.01)
(52) U.S. Cl.
USPC ........................... 250/287; 250/281; 250/282
(58) Field of Classification Search
USPC ................. 250/306, 307, 309, 310, 311, 281, 250/282, 286, 287; 850/1, 2, 3, 5, 21, 52, 850/62, 63
See application file for complete search history.

(56) References Cited

U.S. PATENT DOCUMENTS

| | | | |
|---|---|---|---|
| 5,061,850 A * | 10/1991 | Kelly et al. | 850/1 |
| 5,347,132 A | 9/1994 | Holzman et al. | |
| 5,440,124 A | 8/1995 | Kelly et al. | |
| 6,740,872 B1 | 5/2004 | Holle | |

(Continued)

FOREIGN PATENT DOCUMENTS

| EP | 0231247 A1 | 7/1986 |
|---|---|---|
| EP | 1016123 A1 | 9/1998 |

(Continued)

OTHER PUBLICATIONS

Cerezo et al., (1998) *Rev. Sci. Instrum.*, 69:49-58.

(Continued)

*Primary Examiner* — Nicole Ippolito
(74) *Attorney, Agent, or Firm* — Craig A. Fieschko, Esq.; DeWitt Ross & Stevens S.C.

(57) ABSTRACT

Aspects of the present invention are directed generally toward atom probe and three-dimensional atom probe microscopes. For example, certain aspects of the invention are directed -toward an atom probe or a three-dimensional atom probe that includes a sub-nanosecond laser to evaporate ions from a specimen under analysis and a reflectron for reflecting the ions. In further aspects of the invention, the reflectron can include a front electrode and a back electrode. At least one of the front and back electrodes can be capable of generating a curved electric field. Additionally, the front electrode and back electrodes can be configured to perform time focusing and resolve an image of a specimen.

25 Claims, 4 Drawing Sheets

(56) References Cited

U.S. PATENT DOCUMENTS

| | | | |
|---|---|---|---|
| 6,797,952 B2 | 9/2004 | Kaito et al. | |
| 8,134,119 B2 * | 3/2012 | Panayi | 250/281 |
| 2007/0029473 A1 | 2/2007 | Verentchikov | |

FOREIGN PATENT DOCUMENTS

| | | | |
|---|---|---|---|
| EP | 1124129 A1 | | 8/2001 |
| GB | 2274197 | * | 7/1994 |
| GB | 2274197 A | | 7/1994 |
| GB | 2371143 | * | 7/2002 |
| WO | WO 87/00682 A1 | | 7/1986 |
| WO | WO 99/14793 A1 | | 9/1998 |
| WO | WO 2005003731 A2 | | 7/2004 |
| WO | WO 2005104307 A1 | | 8/2004 |
| WO | WO 2005122210 A1 | | 8/2004 |

OTHER PUBLICATIONS

Liu et al., (1991) *Surface Science*, 246:157-162.

Gault et al., (2005) "Estimation of the tip field enhancement on a field emitter under laser illumination," *Appl. Phys. Letts.*, 86:094101.

Miller et al., (1996) "Atom Probe Field Ion Microscopy," *OUP*, pp. 24-25 and 256-267.

Cerezo et al., (1998) Performance of an energy-compensated three-dimensional atom probe, *Rev. Sci. Instrum.*, 69(1):49-58.

Scherer et al., (2006) A novel principle for an ion mirror design in time-of-flight mass spectrometry, *International Journal of Mass Spectrometry*, 251:73-81.

\* cited by examiner

ATOM PROBE

CROSS-REFERENCE TO RELATED APPLICATIONS

This application claims the benefit of UK Patent Application No. GB0512411.0, filed 17 Jun. 2005, and GB0514216.1, filed 11 Jul. 2005, each of which is fully incorporated herein by reference.

BACKGROUND

Atom probes and three-dimensional atom probes are used for examining the structure of materials, particularly metals and semiconductors, at an atomic scale. Atom probes yield compositional information about the material, while three-dimensional atom probes also provide spatial information about the original atomic positions (e.g. resolving an image of a specimen).

A three-dimensional atom probe removes individual atoms from the surface of a needle shaped specimen with a small tip radius. The individual atoms are ionized and the ions are accelerated towards a position sensitive detector. The detector electronics measure the position at which each ion hits the plate and also calculates the mass/charge ratio of the resulting ion by measuring the time-of-flight (TOF) of the ion from the specimen to the detector.

Three-dimensional atom probes, and their relationship to atom probes generally, are disclosed in the publication 'Atom Probe Field Ion Microscopy' by M. K. Miller, A. Cerezo, M. G. Hetherington and G. D. W. Smith, OUP 1996, which is fully incorporated herein by reference.

EP1016123 A1 and EP0231247 A1, each of which is fully incorporated herein by reference describe atom probes and counter electrode configurations. EP1124129 A1, which is fully incorporated herein by reference, describes a device and method for two-dimensional detection of particles or electromagnetic radiation. U.S. Pat. No. 5,061,850, which is fully incorporated herein by reference, describes a high-repetition rate position sensitive atom probe. U.S. Pat. No. 5,347,132, which is fully incorporated herein by reference, describes a position sensitive detector. U.S. Pat. No. 5,440,124, which is fully incorporated herein by reference, describes a high mass resolution local electrode atom probe.

In order to identify the species of the atoms, the three-dimensional atom probe functions as a mass spectrometer. An electronic detector which measures both the position of the ion and its time of arrival in the same manner as a time of flight (TOF) mass spectrometer enabling elemental identification as well as their original position. In a voltage-pulsed atom probe the atoms at the apex of the specimen are field evaporated by applying short duration pulses to the specimen or electrode.

In a three-dimensional atom probe, ions from the specimen are emitted from an area of the tip which depends on the curvature. They are emitted approximately radially to the tip curvature. A detector is located typically 80 to 600 mm from the tip. The detector is typically square or circular, and has a width in the order of 40 to 100 mm.

In the conventional 3-dimensional atom probe a high voltage is applied to a needle shaped specimen in an ultra-high vacuum environment. A voltage pulse is then applied either to the specimen or to a nearby electrode which raises the electric field at the specimen tip beyond the threshold at which atoms of the specimen become ionized and are accelerated away from the specimen towards a position sensitive and time sensitive detector. The position and chemical identity of the original atoms are then determined and over many such events a three dimensional model of the specimen is reconstructed with atomic resolution.

In certain situations, the use of a voltage pulse can have a number of disadvantages. These include difficulties in analyzing poorly conducting or insulating materials and an inherent energy uncertainty which derives from the trajectory of the accelerating ion through a time-varying electric field coupled with an uncertainty of the precise moment of ionization.

As indicated above, the voltage pulsing technique is generally limited to highly conductive specimens. Energy compensation is often required to achieve higher mass resolution because of energy variations in the evaporated ions. This is particularly important where similar masses are present in widely differing abundances. There are at least three methods for energy compensation. One method involves post acceleration. In one application of this method a pulse is applied to an accelerating electrode which is positioned very close to the specimen. This means that absolute energy variations due to the pulse are reduced because a smaller pulse voltage can be used. The ions are then accelerated before passing into the mass spectrometer part of the atom probe. This means that the relative energy errors are made smaller. Full Width Half Maximum (FW0.5M) resolution is still limited to the order of 500 to 700 in practical designs. U.S. Pat. No. 5,440,124 describes a high mass resolution local electrode atom probe.

A second method is post deceleration. This can involve the use of a double electrode arrangement close to the specimen coupled with a fairly wide pulse and achieves a time focusing effect at the detector by decelerating early ions more than later ones. This is described in WO 99/14793, which is fully incorporated herein by reference.

A third method involves the use of a reflectron in an atom probe or three-dimensional atom probe, which provides very good energy compensation over the entire mass range. The reflectron effectively acts as an electrostatic 'mirror', and alters the direction of an ion which has been field evaporated. The ion is diverted from its initial direction originating from the specimen to a detector. The reflectron can increase the mass resolution of the three-dimensional atom probe in a similar way to its use in a TOF mass spectrometer. A conventional reflectron is formed of a series of ring electrodes, which define a hollow cylinder. The electrodes are each held at an electric potential, the potential increasing in a direction of travel of an ion from an ion source. The electrodes generate a uniform field over the cross-section of the reflectron.

The flatness of the fields can be a key design criterion for conventional reflectrons. Any residual curvature of the fields, which is difficult to avoid, leads to aberrations in ion trajectories and degradation in mass resolution. The ions travel in a parabolic path through the reflectron. Ions with more kinetic energy travel farther into the reflectron, hence their path length is longer and their transit time to the detector is longer. Ions with less kinetic energy do not travel as deep, traverse a shorter path, and have shorter transit times. It can be deduced that ions with a given mass-to-charge ratio and varying kinetic energies will have less variation in their transit time, hence the measured mass resolution will be improved. The reflectron can be configured such that the time taken by the ion to travel through the atom probe is substantially independent of the initial energy of the ion. This is known as time focusing. Conventional designs are limited in the acceptance angle over which they can work. Reflectrons are generally described in Cerezo et al., Rev. Sci. Instrum. 69 (1998) (see e.g., pages 49-58), which is fully incorporated herein by reference.

Ions liberated with the same mass-to-charge ratio but slightly different kinetic energies will follow different trajectories through the reflectron and will strike the detector at slightly different locations. The spread of impact positions is proportional to the chromatic aberration of the system. In addition, as the field of view (FOV) increases so does the chromatic aberration.

Laser pulses may be used instead of, or in addition to, voltage pulsing to stimulate ion evaporation. This is particularly useful for non-conducting or poorly conducting specimens such as semiconductors and oxides. Transient surface heating and bulk heating of the specimen, which effectively lengthens the period over which evaporation occurs, can degrade mass resolution. In some cases the high temperatures achieved lead to diffusion of atoms in the specimen and thus a loss of spatial resolution.

Laser pulsing is described in Liu, C. Wu and T. T. Tsong, Surface Science, 246 (1991) (see e.g., 157-162), which is fully incorporated herein by reference. High FW0.5M resolutions were obtained (only with long flight path and hence narrow FOV but Full width Tenth, Hundredth and Thousandth maximum resolutions were limited by exponential tails.

SUMMARY

Aspects of the present invention relate to atom probe and three-dimensional atom probe microscopes. For example, certain aspects of the invention are directed toward an atom probe or a three-dimensional atom probe that includes a sub-nanosecond laser to evaporate ions from a specimen under analysis and a reflectron for reflecting the ions. In further aspects of the invention, the reflectron can include a front electrode and a back electrode. At least one of the front and back electrodes can be capable of generating a curved electric field. Additionally, the front electrode and back electrodes can be configured to perform time focusing and resolve an image of a specimen.

BRIEF DESCRIPTION OF THE DRAWINGS

Several specific details of the invention are set forth in the following description and in FIGS. 1-8 to provide a thorough understanding of certain embodiments of the invention. One skilled in the art, however, will understand that the present invention may have additional embodiments, and that other embodiments of the invention may be practiced without several of the specific features described below.

DETAILED DESCRIPTION

Aspects of the present invention relate to atom probe and three-dimensional atom probe microscopes. For example, certain embodiments of the present invention include an atom probe or a three-dimensional atom probe comprising:
(i) a sub-nanosecond laser (e.g., a picosecond or femtosecond laser) to at least aid in evaporating ions from a specimen under analysis, and
(ii) a reflectron.

In selected embodiments, the atom probe can be particularly useful for analyzing materials which are not highly conductive such as semiconductors and oxides.

In selected embodiments, the sub-nanosecond laser can include a femtosecond laser or the like. Experiments have been undertaken using green light ($\lambda$=515 nm) at 10 kHz pulsing and 100 kHz pulsing in conjunction with a half-wave plate polarizer. The laser power was on the order of 50 mW. A sub-picosecond (e.g., a femtosecond laser) is described in B. Gault, F. Vurpillot, A. Bostel, A. Menand, B. Deconihout, Appl. Phys. Letts. 86 (2005) 094101, which is fully incorporated by reference.

In selected embodiments, the laser can be focused to a spot at the apex of the specimen. An optics system can be fitted to focus the laser onto the tip and a camera is can be incorporated for alignment purposes (see e.g., PCT Patent Application Nos. WO2005122210 and WO2005104307, each of which is fully incorporated herein by reference). One method of laser pulsing is described in WO2005003731, which is fully incorporated herein by reference.

The reflectron can include a wide angle reflectron as herein described. Conventional atom probe reflectrons accept about an 8 degree cone. Accordingly, in selected embodiments a suitable reflectron can have an acceptance angle of >8 degrees, thus enabling a wider FOV to be analyzed. A wider FOV results in a larger analysis volume thus allowing analysis of features such as transistor gates and other significant structures.

In selected embodiments, it is expected that a short sub-nanosecond laser pulse may reduce surface and/or bulk heating of the specimen and in some case improve analysis characteristics over present systems. Additionally, in certain embodiments the longer path length (hence longer TOF when compared to a linear flight path configuration) possible with the reflectron may further enhance mass resolution and the energy compensation properties of the reflectron, greatly reducing the energy variations of the evaporated ions.

Experiments have been carried out with a femtosecond laser with a pulse width of 400 femtoseconds and a pulse energy of a few microjoules. A reflectron was incorporated into the instrument. The reflectron effectively eliminated any exponential mass tails resulting in full width half maximum resolution of 2000 and full width $\frac{1}{1000}^{th}$ maximum resolution of 500 (full width half maximum: this means the ratio of the mass to the width of the spectrum peak at half its maximum value).

Accordingly, certain embodiments of the present invention enable higher mass resolutions to be achieved and are directed to an atom probe comprising a combination of a sub-nanosecond laser in conjunction with a reflectron. In particular, one embodiment uses a femtosecond laser to evaporate specimens in an atom probe, which further comprises a wide-angle reflectron. This combination of a femtosecond laser and a reflectron can result in a very high mass resolution. For example, a Full Width $1/1000^{th}$ maximum resolution of 500 has been achieved.

The atom probe or a three-dimensional atom probe will typically further comprise a detector for detecting ions. Conventional detectors may be used. Detectors are described in EP 1016123 A1, EP 0231247 A1 and EP 1124129 A1.

The reflectron of the present invention can be configured such that the time taken to travel through the three-dimensional atom probe, including the time spent in the reflectron, is independent of the initial energy of the ion. This is known as time focusing, and improves the mass resolution of the spectrometer. A reflectron suitable for certain embodiments of the invention is described in our patent application GB 0509638.3 and PCT application PCT/GB2006/001694, entitled Curved Reflectron, filed May 10, 2006, both of which are fully incorporated herein by reference. The reflectron effectively acts as an electrostatic 'mirror', and reverses the direction of an ion which is being analyzed in the mass spectrometer. The ion is reflected from its initial direction from an ion source onto a detector. The reflectron can increase the mass resolution of the three-dimensional atom probe in a similar way to its use in a time-of-flight mass spectrometer. A conventional reflectron is formed of a series of ring electrodes, which define a hollow cylinder. The electrodes are each held at a different electric potential, the potential increasing in a direction of travel of an ion from an ion source. The electrodes generate a uniform field over the cross-section of the reflectron. The ions travel in a parabolic path through the reflectron.

The ion source in a three-dimensional atom probe is a specimen under examination with a curved surface of small dimensions. The ions originate from a small area of the surface and proceed towards a detector plate at some distance away. They thus form an image on the detector of the specimen area at a very large magnification. A conventional reflectron used in an atom probe has the disadvantage that an angle spread of more than approximately 8 degrees results in an excessively large reflectron and detector or alternatively an excessively short flight path.

A conventional reflectron used in an atom probe has the disadvantage that the location of reflected images depends on the energy of the ions. When there is an energy spread of the ions, as occurs in voltage-pulsed atom probes for example, the resultant reflected image is blurred in a direction away from the reflectron normal by the amount of displacement that the energy spread introduces. Furthermore, the displacement magnitude increases with angle from the reflectron normal so that reflectrons which pass large fields of view will have a large blurring at large acceptance angles. This effect is known as chromatic aberration which is a spread in the position of the detected ions dependent on the energy spread of the ions.

In certain embodiments, it is desirable that a reflectron used in a three-dimensional atom probe be able to accept ions over a significantly larger range of angles than a reflectron in a time-of-flight mass spectrometer in order to yield a wide FOV. Certain reflectrons designed for use in an atom probe or a time-of-flight mass spectrometer may not be suitable for use in a three-dimensional atom probe if they will only accept and reflect ions incident over a small range of angles.

Accordingly, a reflectron for use in selected embodiments of the present invention can comprise:
a front electrode; and
a back electrode;
wherein at least one of the front and back electrodes is capable of generating a curved electric field;
the front electrode and back electrodes being configured to perform time focusing and resolve an image of a specimen.

In certain embodiments, the reflectron for use in the present invention has improved space angle focusing of the ions over a wide range of angles. The reflectron may also be configured to reduce or almost eliminate chromatic aberration.

In selected embodiments, the front electrode has a concave surface facing the ion source. In some embodiments, the concave surface of the front electrode is curved with a constant radius of curvature.

In certain embodiments, the front electrode may take any suitable form but will typically comprise a mesh.

In selected embodiments the front electrode is held at ground potential.

In certain embodiments, the back electrode is held at a potential of at least approximately 1.08 times the mean energy of ions to be reflected.

In selected embodiments, the back electrode has a concave surface facing the ion source. In some embodiments, the concave surface of the back electrode is curved with a constant radius of curvature.

In certain embodiments, the back electrode may take any suitable form but will typically comprise a plate.

In selected embodiments, when the reflectron is incorporated in a three-dimensional atom probe, the radius of curvature of the front electrode is substantially equal to the distance between the front electrode and a detector for detecting ions in the three-dimensional atom probe. In some embodiments, the radius of curvature of the back electrode is substantially equal to the distance between the back electrode and the detector for detecting ions in the three-dimensional atom probe.

In certain embodiments, a radius of curvature of the front electrode and a radius of curvature of the back electrode are such that the two electrodes are concentric.

In selected embodiments, the reflectron also contains a plurality of intermediate electrodes disposed between the front electrode and the back electrode. Each of the intermediate electrodes can be formed as an annulus.

In certain embodiments, each of the intermediate electrodes is held at an electric potential equivalent to the potential at their location which would be generated by the point charge simulated by the front electrode and back electrode.

In selected embodiments, the front electrode has a concave surface having a constant radius of curvature, the radius of curvature of the front electrode being substantially equal to the distance between the front electrode and a detector for detecting ions in said atom probe. In some embodiments, the back electrode has a concave surface having a constant radius of curvature, the radius of curvature of the back electrode being substantially equal to the distance between the back electrode and a detector for detecting ions in said atom probe.

In selected embodiments the front electrodes, back electrodes, and detector can be configured to yield a time of flight that is greater than one microsecond and/or yield an effective path length of 100-800 mm. Furthermore, for a given FOV the curved reflectron can allow a longer flight path length than a linear projection. This means that higher mass resolution, resulting from decreased timing uncertainty, is possible with the curved reflectron geometry.

Generally, the reflectron substantially reverses the direction of the ions, by generating an electric potential greater than the energy equivalent of the ion. An ion generally enters the reflectron at an angle to a radius line of the electrodes, so that the ion travels in an ellipse through the reflectron. The detector is offset from a path of the ions from their source to the reflectron. In the limiting case of the conventional planar reflectron, the radius becomes the longitudinal axis of the reflectron and the ellipse becomes a parabola.

The surface atoms are field evaporated by, for example, applying short pulses of higher voltage to the specimen. However, in selected embodiments of the present invention the electric field is held static (or essentially static) and a laser is pulsed to provide energy for evaporation. In selected embodiments, the laser can include a femtosecond laser having a pulse length less than 1 picosecond. Experiments have been undertaken using green light ($\lambda$=515 nm) at 10 kHz pulsing and 100 kHz pulsing in conjunction with a half-wave plate polarizer. The laser power was typically on the order of 50 mW.

In certain embodiments of a three-dimensional atom probe, ions from the specimen are emitted from an area of the tip which depends on the curvature. They are emitted approximately radially to the tip curvature. A detector can be located 100 to 600 mm from the tip. The detector can be square or circular, and can have a width in the order of 40 to 100 mm.

There can be an image area on the tip of the specimen from which ions emitted from the specimen will strike the detector. The ratio of the linear dimensions of the detector and image area on the specimen is termed the magnification. The magnification is typically too large for optimum analysis of the specimen so it needs to be reduced. The magnification can be reduced by reducing the detector distance; by increasing the tip radius or by increasing the detector size. Often, for practical reasons, the detector is limited in size; the tip radius is limited to between 50 and 100 nm, and the detector distance needs to be as large as possible. Thus, one way to achieve a magnification decrease is to accept a fairly wide cone angle of emitted ions from the tip. This means however that a reflectron must function with a wide range of input angles. In many cases, 30 degrees or more would be desirable. For a conventional planar reflectron however the performance degrades both in mass resolution terms and from the point of view of chromatic aberration if the cone angle is much greater than 8 degrees. This also means that the detector distance would be undesirably short.

Figure 1:
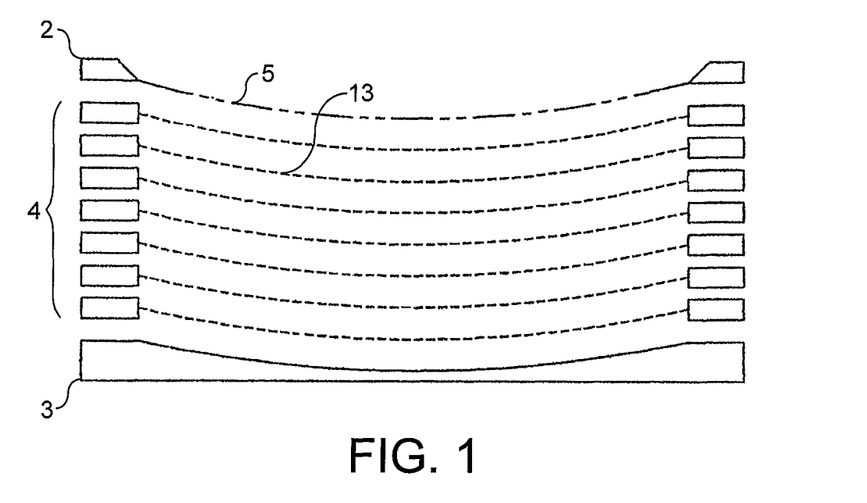
FIG. 1 is a plan view of a reflectron for use in one embodiment of the present invention showing lines of equal electric potential.
Figure 2:
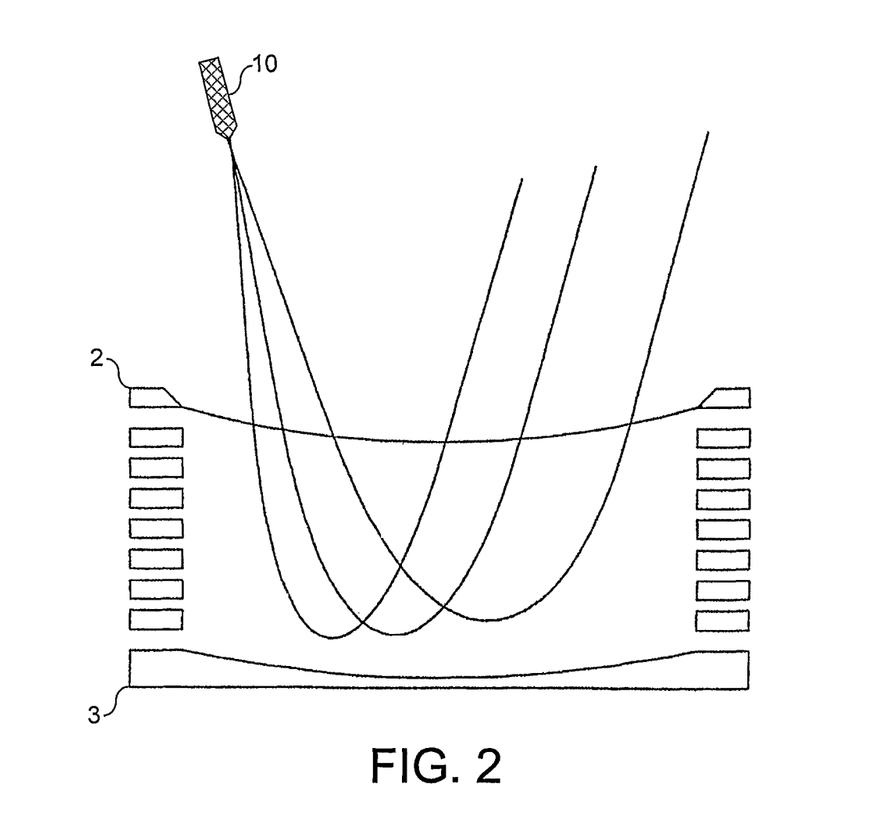
FIG. 2 is a plan view of a reflectron for use in one embodiment of the present invention showing example paths of ions.

With reference to FIGS. 1 and 2, a reflectron 1 for use in one embodiment of the present invention comprises a curved front electrode 2. The front electrode 2 is formed in the shape of part of a sphere, such that it has a constant radius of curvature. The front electrode 2 has a concave side 6 and a convex side 7, and has a diameter of approximately 40 mm to 200 mm. The front electrode 2 is comprised of a fine mesh or grid. The mesh allows approximately 90% of incident ions to pass through.

In the illustrated embodiment, a plurality of annular electrodes 4 are arranged behind the front electrode 2, on the convex side 7 of the front electrode 2. The annular electrodes 4 do not incorporate a mesh, but are ring shaped with a central circular aperture through which the ions can freely pass. The number of these electrodes, their spacing and the voltages on them can vary with the specific design.

In FIGS. 1 and 2, a back electrode 3 is located at the opposite end of the reflectron 1 from the front electrode 2. The back electrode 3 is spaced apart from the front electrode 2 by typically 40 to 100 mm. This distance depends on many factors according to the magnification and time focusing requirements. In the illustrated embodiment, the annular electrodes 4 are thus intermediate the front electrode 2 and back electrode 3.

The back electrode 3, in FIGS. 1 and 2, is aligned along a longitudinal axis of the reflectron 1 with the front electrode 2 and annular electrodes 4. The back electrode 3 has an upper surface 5 which is curved in the shape of part of a sphere. In the illustrated embodiment, the upper surface 5 of the back electrode 3 is concentric with the front electrode 2 and thus has a constant radius of curvature which is greater than the radius of curvature of the front electrode 2. The upper surface 5 is concave, the concave surface 5 facing towards the front electrode 2.

With reference to FIG. 2, the concave side 6 of the front electrode 2 and the concave upper side 5 of the back electrode 3 are oriented approximately towards an ion source 10.

In selected embodiments, the radius of curvature of the front electrode 2 is equal to or smaller than the radius of curvature of the back electrode 3.

For example, in certain embodiments the radius of curvature of the front electrode 2 may be approximately the same as the distance between a detector and the front electrode 2. The radius of curvature of the upper surface 5 of the back electrode 3 may be substantially the same as the distance between the detector and the back electrode 3. The front electrode 2 and the upper surface 5 can each be shaped as a part of spheres which may have their centres in proximity to the detector. This arrangement can allow the reflectron 1 to spatially focus the ions onto the detector.

Figure 3:
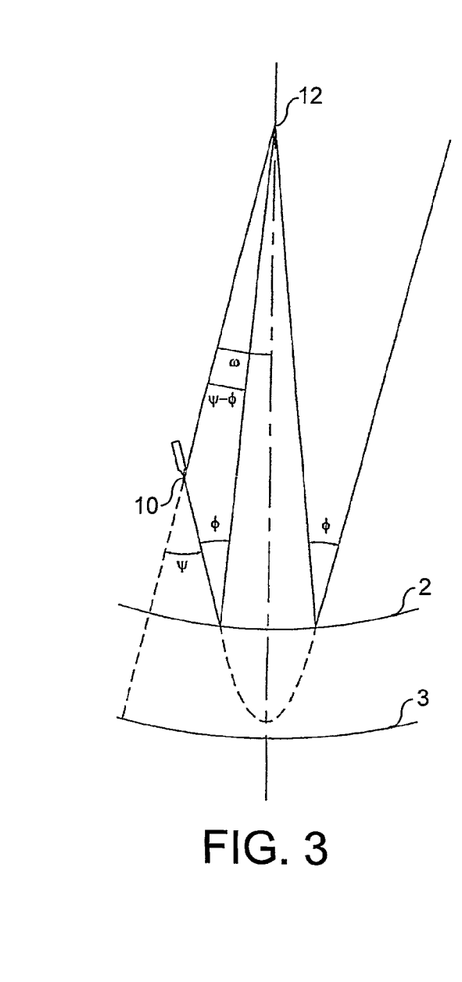
FIG. 3 is a plan view of a reflectron for use in one embodiment of the present invention showing an example path of an ion.

With reference to the embodiment illustrated in FIG. 3, the reflectron 1 achieves spatial focusing of the ions onto a detector when an entry angle $\psi$ is up to approximately 45°. The reflectron 1 is able to reduce the magnification of the three-dimensional atom probe such that the image on the detector corresponds to a much larger area of the specimen. The point 12 is the centre of the spheres of the electrodes 2,3, and the focus of the elliptical path followed by the ions.

Figure 4:
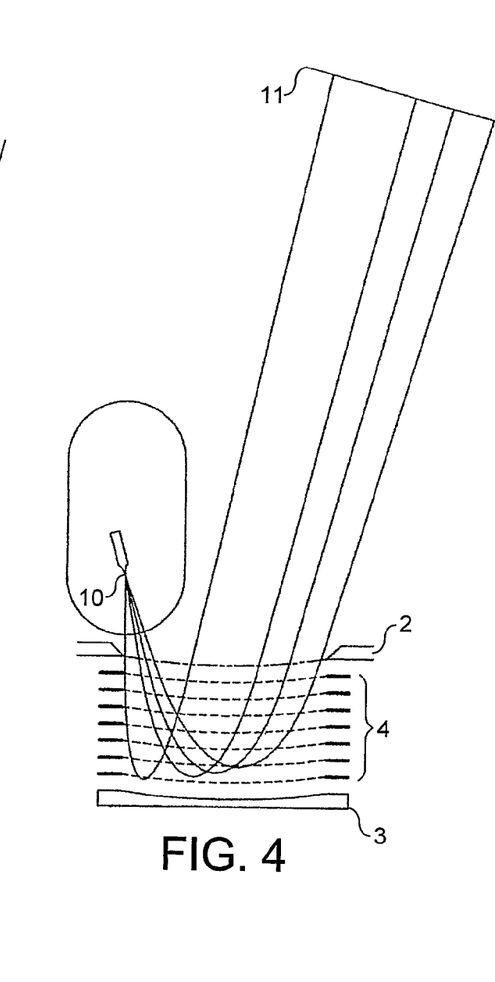
FIG. 4 is a plan view of a reflectron for use in one embodiment of the present invention showing paths of ions with different initial ion trajectories.

FIG. 4 is a plan view of a reflectron for use in one embodiment of the present invention showing the different ion trajectory geometries. Within the reflectron 1, the ion follows an elliptical path. A focus of the ellipse is at the centre of curvature of the electrodes. Analytic expressions exist for the major and minor diameters of the ellipse, and the other angles shown for given reflectron parameters and for each angle that the incident ion path makes with a datum line between the specimen tip and the centre of curvature. FIG. 4 shows the position of the detector 11.

In the illustrated embodiment, the reflectron 1 achieves substantially linear space angle focusing of the ions over a wide range of angles, and so is able to reduce the magnification of the three dimensional atom probe such that the image on the detector corresponds to a much larger area of the specimen. The relationship between the angle at which an ion is emitted from the ion source 10, and the position on the detector 11 is linear. This means that the image produced by the detector 11 corresponds to the specimen with negligible distortion.

In one embodiment, the trajectories in all the figures are calculated from analytic expressions. Analytic expressions are also available for the time the ion spends in the reflectron and the derivative of the time with ion energy. The latter is used to determine the reflectron parameters used to calculate the above trajectories.

Figure 5:
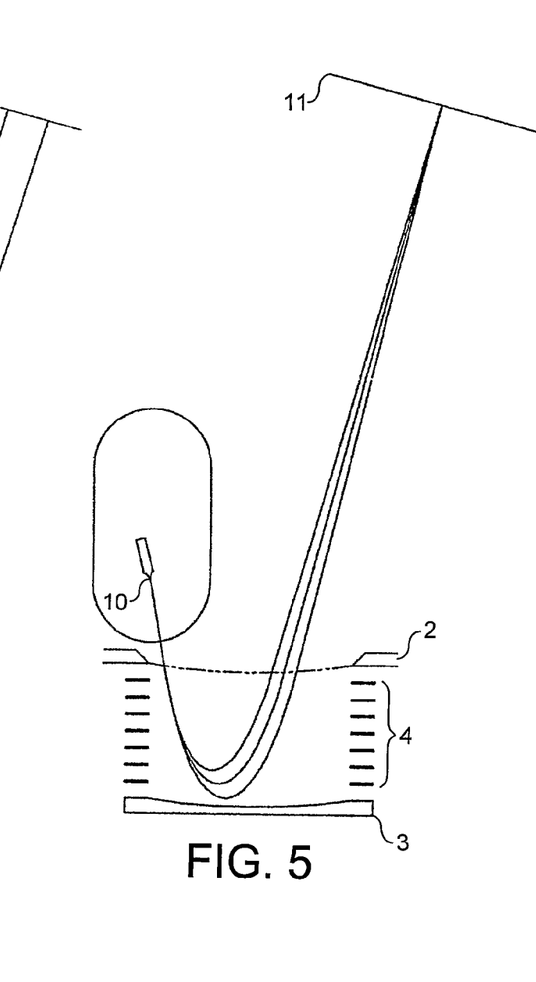
FIG. 5 is a plan view of a reflectron for use in one embodiment of the present invention showing paths of ions with different initial energies.

FIG. 5 shows example paths of ions emitted at the same angle from the specimen with a range of initial energies in accordance with one embodiment of the invention. The ions shown have an exaggerated energy variation in the range of +/−10%. Typically, an energy variation in the range +/−0.1% would be expected.

The ability of the reflectron 1 to focus ions of different energies onto substantially the same position on the detector reduces chromatic aberration in the illustrated embodiment. When the centre of the spheres defined by the front electrode and back electrode are in the same plane as the detector, chromatic aberration can be substantially eliminated.

In the illustrated embodiment, the reduction in chromatic aberration is possible because the lateral shift in exit position of the ion due to an energy change can be compensated for by the change in exit angle caused by the same energy variation. This can occur when the centre of curvature of the electrodes is near to the position of the detector but other configurations are possible. With reference to FIG. 3, the entry angle Φ is the same as exit angle Φ, which indicates that the position of the ion on the detector is not substantially dependent on the energy of the ion.

The reflectron 1, in the illustrated embodiment, can accept ions diverging over a relatively large angle. The angle for which the reflectron 1 can perform time focusing and substantially linear spatial focusing of ions with substantially eliminated chromatic aberration is approximately three times greater than for a conventional uniform field reflectron. The reflectron 1 may be smaller than a conventional uniform field reflectron of the same diameter and for the same effective flight distance and still achieve time focusing.

In selected embodiments, an electric potential is applied to the front electrode 2, back electrode 3 and annular electrodes 4. The potential applied to the back plate 3 is greater than the equivalent energy of the ions which are to be measured. This ensures that the ions are reflected back towards the source of the ions before they reach the back electrode 3.

In the illustrated embodiment, the potentials applied to all the electrodes are calculated to ensure that the field within the reflectron is always directed radially away from the centre of curvature. The annular electrodes maintain the correct potentials to minimize the edge effect caused by the fact that the front and back electrodes are only partial spheres.

In selected embodiments the intermediate, annular electrodes 4 are spaced and held at appropriate voltages to ensure that the field inside the reflectron is as closely as possible equivalent to that which would be generated by a theoretical point charge of suitable value located at the centre of curvature. The annular electrodes 4 are each held at the potential which would be present at their location due to the point charge which the reflection 1 aims to simulate.

In the illustrated embodiment, the equipotential field lines 13 are curved and substantially in the shape of part of a sphere. The field generated by the reflectron 1 approximately mimics the field which would be generated by a point charge located at the centre of the spheres defined by the front and back electrodes. The centre of the spheres defined by the front and back electrodes can be in proximity to the detector. The centre of the spheres defined by the front and back electrodes may be at approximately the same distance from the electrodes 2,3 as the detector is from the respective electrodes 2,3. In selected embodiments, the centre of the spheres defined by the front and back electrodes will not coincide with the detector, if the detector is offset from the axis of the electrodes 2,3. Since the reflectron 1 substantially simulates a point charge, ions in the reflectron move in an ellipse.

In FIG. 5, an ion from the ion source 10 first passes through the mesh of the front electrode 2. The path of the ion is altered by the non-uniform electric potential it experiences. The ion passes through the central aperture of at least some of the annular electrodes 4. The electric potential the ion continues to experience within the reflectron 1 causes its speed in the direction of an axis of its elliptical orbit to reduce to zero, before the ion reaches the back plate 3. The electric potential applied to the back plate 3, annular rings 4 and front electrode 2 causes the ion to accelerate back towards the front electrode 2 and away from the back plate 3. The ion then passes back through the annular electrodes 4 and front electrode 2 and continues until it hits the detector.

In the illustrated embodiment, the time taken by the ion to travel from a point adjacent the ion source to the detector is measured, and used to calculate the mass/charge ratio of the ion. The identity of the ion is determined by reference to known values for the mass/charge ratio of ions.

In certain embodiments, the mesh is at ground potential and the back electrode is held at a potential equal to approximately 1.08 times the nominal energy of the ions. The annular electrodes are held at intermediate potentials between the potential of the front electrode 2 and back electrode 3. The potential of the annular electrodes 4 increases towards the back electrode 3. In selected embodiments, the potentials of the annular electrodes 4 are calculated to maintain a substantially radial field at the edges of the reflectron 1. The annular electrodes thus compensate for the front and back electrodes 2,3 forming only part of a sphere, and not a complete sphere.

In FIG. 5, the front electrode is described as a mesh or grid. Alternatively, in other embodiments it may be formed from a solid material with holes or may be replaced by an electrostatic lens arrangement consisting of further annular electrodes held at different voltages.

Although in the illustrated embodiment the back electrode is described as spherically curved, in other embodiments the back electrode could also have a different type of curvature or be planar. In still other embodiments the curvature of the front electrode could also not be constant. In some embodiments the shape of the front electrode can have a greater effect on an ion trajectory than the back electrode, and so in selected embodiments a planar back electrode could be utilized. Alternatively, in other embodiments a planar front electrode could be used with a curved back electrode. The front electrode and back electrode are therefore not necessarily concentric.

In the illustrated embodiment, the centres of the spheres defined by the front electrodes and back electrodes have been described as being adjacent to or in proximity to the detector. Alternatively, in other embodiments the centre of the spheres defined by the front electrodes and back electrodes may be located away from the detector. Thus, the radius of curvature of the front electrode and/or the rear electrode does not necessarily substantially equal the distance from that electrode to the detector.

Figure 6:
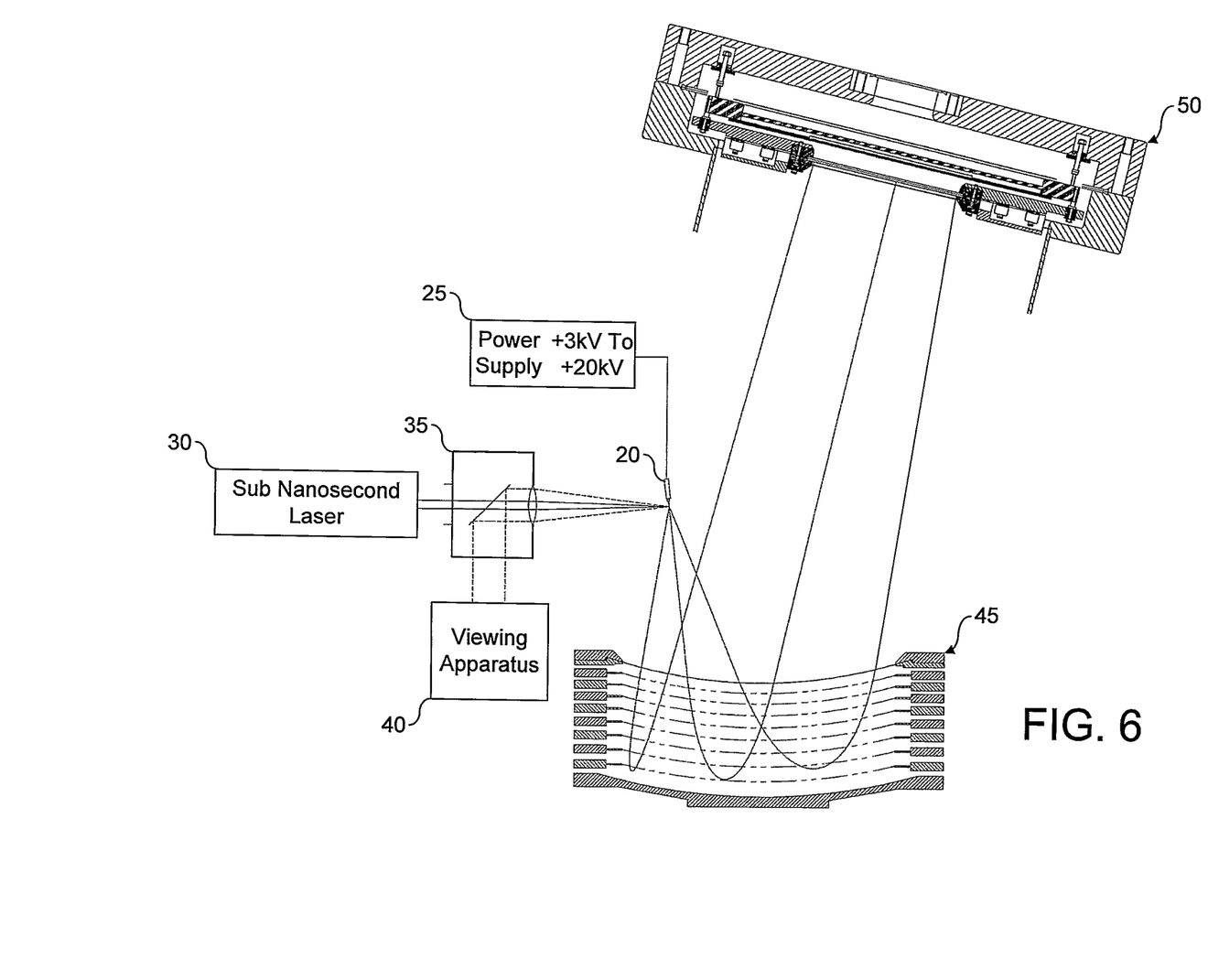
FIG. 6 shows a schematic diagram of an atom probe according to one embodiment of the present invention which incorporates a wide angle reflectron.

FIG. 6 shows a schematic diagram of an atom probe according to one embodiment of the present invention which incorporates a wide angle reflectron. The specimen (e.g. semiconductor material) 20 is electrically coupled to a power supply (1-30 kV). The specimen is maintained in a vacuum at a low temperature by conventional means. A sub-nanosecond laser 30 is provided in conjunction with laser optics 35, together with viewing means 40. Accordingly, the laser is focused onto the tip of the specimen 20 and, in use, stimulates ion evaporation during each pulse. The specimen 20 is held at a static or essentially static voltage during this operation. The acceptance angle is the full linear angle bounded by the two outermost ion trajectories with the specimen as the vertex.

In other embodiments the voltage can be pulsed with the laser to provide evaporation energy. Combined voltage and laser pulsing are described in Laser Atom Probes 60/637,912 which is fully incorporated herein by reference.

Figure 7:
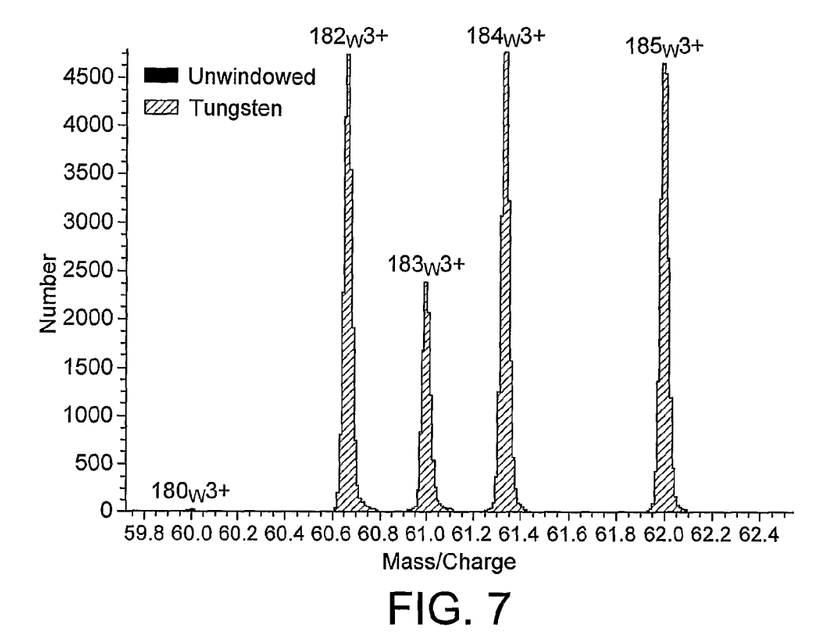
FIG. 7 shows typical mass resolutions obtained with the instrument for a Tungsten specimen in accordance with an embodiment of the invention.
Figure 8:
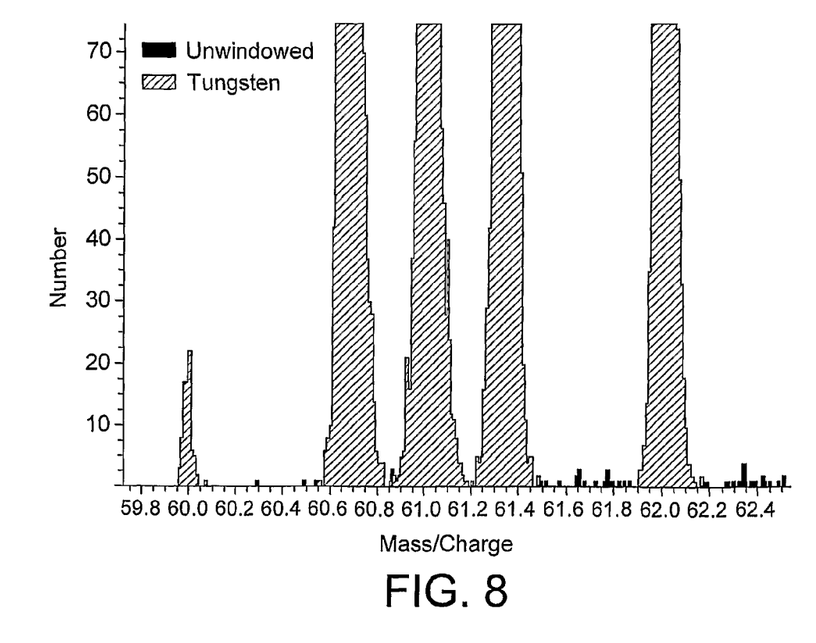
FIG. 8 shows higher mass resolution (on the order of FULL WIDTH $\frac{1}{1000}^{th}$ MAXIMUM (FW0.1% M) obtained with the instrument for a Tungsten specimen in accordance with an embodiment of the invention.

Synchronous electronic timing with each laser pulse is obtained by conventional methods. The evaporated ions from the tip of the specimen then are directed via the reflectron 45 (as herein described) to the detector 50. The detector 50 may be any conventional detector but in selected embodiments is a position sensitive detector. Such a detector, which is well known, detects the position of the ion, which corresponds with the original position of the atom on the specimen surface and, furthermore, measures the mass/charge ratio of the ion by timing the flight of the ion through the atom probe. The trajectories of the evaporated ions are shown in the drawing. FIGS. 7 and 8 shows mass resolutions obtained with the instrument shown in FIG. 6 for a tungsten specimen.

From the foregoing, it will be appreciated that specific embodiments of the invention have been described herein for purposes of illustration, but that various modifications may be made without deviating from the invention. Additionally, aspects of the invention described in the context of particular embodiments may be combined or eliminated in other embodiments. Although advantages associated with certain embodiments of the invention have been described in the context of those embodiments, other embodiments may also exhibit such advantages. Additionally, not all embodiments need necessarily exhibit such advantages to fall within the scope of the invention. Accordingly, the invention is not limited except as by the appended claims.

The invention claimed is:

1. An atom probe including:
   a. a laser to at least aid in evaporating ions from a specimen under analysis;
   b. a reflectron for reflecting the ions, wherein the reflectron includes:
      (1) a front electrode; and
      (2) a back electrode;
   wherein:
      I. at least one of the front and back electrodes is configured to generate a curved electric field along a flight path of the ions; and
      II. the front and back electrodes are configured to perform time focusing and resolve an image of the specimen.

2. The atom probe of claim 1 wherein the front electrode has a concave surface facing the ion source.

3. The atom probe of claim 1 wherein the back electrode has a concave surface facing the ion source.

4. The atom probe of claim 1 wherein the front electrode is curved with a constant radius of curvature.

5. The atom probe of claim 1 wherein the back electrode is curved with a constant radius of curvature.

6. The atom probe of claim 1 wherein:
   a. the front electrode is curved, and
   b. the radius of curvature of the front electrode is substantially equal to the distance between the front electrode and a detector for detecting ions in said atom probe.

7. The atom probe of claim 1 wherein:
   a. the back electrode is curved, and
   b. the radius of curvature of the back electrode is substantially equal to the distance between the back electrode and a detector for detecting ions in said atom probe.

8. The atom probe of claim 1 wherein:
   a. both the front electrode and back electrode are curved, and
   b. a radius of curvature of the front electrode and a radius of curvature of the back electrode are such that the two electrodes are concentric.

9. The atom probe of claim 1 wherein a plurality of intermediate electrodes are disposed between the front electrode and the back electrode.

10. The atom probe of claim 9 wherein each of the intermediate electrodes are held at an electric potential equivalent to the potential at their location which would be generated by the point charge simulated by the front electrode and back electrode.

11. The atom probe of claim 9 wherein each of the intermediate electrodes are formed as an annulus.

12. The atom probe of claim 1 wherein the front electrode is held at ground potential.

13. The atom probe of claim 1 wherein the back electrode is held at a potential of approximately 1.08 times the mean energy of ions to be reflected.

14. The atom probe of claim 1 wherein the front electrode comprises a mesh.

15. The atom probe of claim 1 wherein the back electrode comprises a plate.

16. The atom probe of claim 1 wherein the front and back electrodes are configured such that when an electric potential is applied to at least one of the electrodes an electric field is generated substantially equivalent to an electric field produced by a point charge.

17. The atom probe of claim 1 further comprising a detector for detecting ions.

18. The atom probe of claim 1 wherein the front and back electrodes are configured to provide a spatially-focused image plane onto which the image is resolved, with:
   a. the spatially-focused image plane being at least substantially coincident with a time-focused image plane, and
   b. the image planes being spaced from the electrodes.

19. The atom probe of claim 18 wherein a detector is situated at least substantially coincident with the image planes.

20. An atom probe including:
   a. a laser configured to illuminate a specimen under analysis;
   b. a reflectron situated to receive evaporated ions traveling along an ion flight path from the specimen, wherein the reflectron includes:
      (1) a front electrode situated along the ion flight path, and
      (2) a back electrode spaced from the front electrode, wherein the reflectron is configured to:
         I. generate a curved electric field intersecting the ion flight path,
         II. perform time focusing, and
         III. resolve an image of a specimen.

21. The atom probe of claim 20 wherein the front and back electrodes are configured to provide a spatially-focused image plane onto which the image is resolved, with:
   a. the spatially-focused image plane being at least substantially coincident with a time-focused image plane, and
   b. the image planes being spaced from the electrodes.

22. The atom probe of claim 21 wherein a detector is situated at least substantially coincident with the image planes.

23. An atom probe including:
   a. a laser configured to stimulate ion evaporation from a specimen under analysis;
   b. a reflectron situated to receive evaporated ions traveling along an ion flight path, wherein the reflectron includes at least two electrodes arrayed in a direction along the ion flight path, wherein the electrodes are configured to:
      (1) generate a curved electric field intersecting the ion flight path,
      (2) perform time focusing of the evaporated ions, and
      (3) resolve an image of the specimen from the evaporated ions.

24. The atom probe of claim 23 wherein the electrodes are configured to provide a spatially-focused image plane onto which the image is resolved, with:
    a. the spatially-focused image plane being at least substantially coincident with a time-focused image plane, and
    b. the image planes being spaced from the electrodes.

25. The atom probe of claim 24 wherein a detector is situated at least substantially coincident with the image planes.

\* \* \* \* \*